US007005418B1

(12) United States Patent
Riethmuller-Winzen et al.

(10) Patent No.: US 7,005,418 B1
(45) Date of Patent: Feb. 28, 2006

(54) METHOD FOR THE THERAPEUTIC MANAGEMENT OF EXTRAUTERINE PROLIFERATION OF ENDOMETRIAL TISSUE, CHRONIC PELVIC PAIN AND FALLOPIAN TUBE OBSTRUCTION

(75) Inventors: Hilde Riethmuller-Winzen, Frankfurt (DE); Jurgen Engel, Alzenau (DE); Ricardo Felberbaum, Lubeck (DE); Klaus Diedrich, Gross-Sarau (DE); Wolfgang Küpker, Lubeck (DE)

(73) Assignee: Zentaris GmbH, Frankfurt am Main (DE)

( * ) Notice: Subject to any disclaimer, the term of this patent is extended or adjusted under 35 U.S.C. 154(b) by 705 days.

(21) Appl. No.: 09/666,146

(22) Filed: Sep. 20, 2000

Related U.S. Application Data

(60) Provisional application No. 60/155,478, filed on Sep. 23, 1999.

(51) Int. Cl.
*A61K 38/00* (2006.01)

(52) U.S. Cl. .......................... 514/12; 514/13; 514/14; 514/15; 514/16; 514/17; 514/18; 514/19

(58) Field of Classification Search ............. 514/12–19
See application file for complete search history.

(56) References Cited

U.S. PATENT DOCUMENTS 5,658,884 A   8/1997   Hodgen
5,663,145 A * 9/1997   Engel et al.

FOREIGN PATENT DOCUMENTS

| EP | 0 943 336 A1 | 9/1999 |
|----|----|----|
| WO | WO 97 27863 | 8/1997 |
| WO | WO 98/55470 | 12/1998 |
| WO | WO 00/55190 | 9/2000 |

OTHER PUBLICATIONS

Nachtigall et al., Chapter 41, Danforth's Obstetrics and Gynecology, 1994, p. 757-769.*
Reissmann et al. (Reissmann 1994), "Introduction of LHRH-Antagonists Into The Treatment of Gynaecological Disorders," Human Reproduction, vol. 9, No. 5, pp. 767-769 (1994).*

(Continued)

*Primary Examiner*—San-Ming Hui
(74) *Attorney, Agent, or Firm*—Pillsbury Winthrop Shaw Pittman LLP

(57) ABSTRACT

The present inventions provides a method for therapeutic management of extrauterine proliferation of endometrial tissue, chronic pelvic pain and fallopian tube obstruction by short term induction treatment with an LH-RH antagonist for 4 to 12 weeks. According to another aspect of the present invention, the short term LH-RH treatment is followed by the combined or separate administration of one or more active agents selected from the group consisting of a contraceptive, preferably an oral contraceptive, a non-steroidal anti-rheumatic agent, an analgetic, an androgen other than a 17-alpha-alkyl substituted testosterone or any combinations thereof. According to a further aspect of the present invention a pharmaceutical composition comprising an LHRH antagonist and one ore more active agents selected from the group consisting of a contraceptive, preferably an oral contraceptive, a non-steroidal anti-rheumatic agent, an analgetic, an androgen other than a 17-alpha-alkyl substituted testosterone or any combinations thereof are provided.

17 Claims, 2 Drawing Sheets

Figure 1:
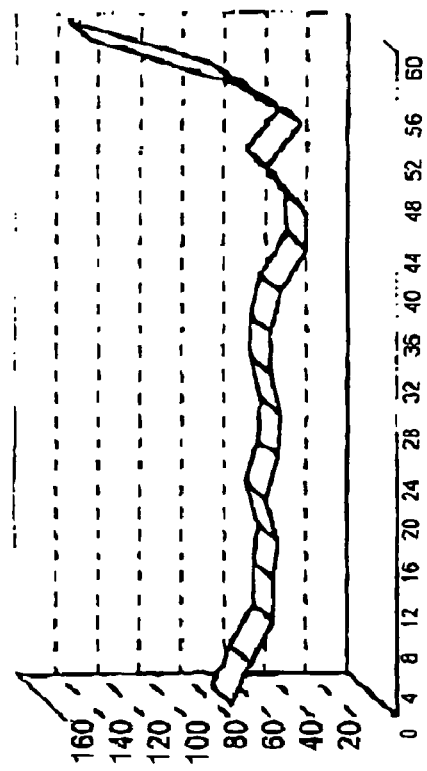

CTT in Endometriosis
estradiol [pg/ml]

Cetrorelix in patients with endometriosis 3 mg cetrorelix per week starting on cycle day one to three
Estradiol serum levels during 8 weeks therapy

OTHER PUBLICATIONS

Reissmann et al. (Reissmann 1995), "Development and Applications of Luteinizing Hormone-Releasing Hormone Antagonists in the Treatment of Infertility: An Overview," Human Reporudction, vol. 10, No. 8, pp. 1974-1981 (1995).*

Kettel et al. (Kettel), "Rapid Regression of Uterine Leiomyomas in Response to Daily Administration of Gonadotroin-Releasing Hormone Antagonist," Fertility and Sterility, vol. 60, No. 4, pp. 642-646 (1993).*

Norman, P., "Cetrorelix, ASTA Medica AG", Current Opinion in Oncologic, Endocrine & Metabolic Investigational Drugs, vol. 2, No. 2, pp. 227-248, XP-000982761.

Th. Reissmann et al., Human Reproduction vol. 10, No. 8, pp. 1974-1981.

International search report.

Smetnik et al., Nonsurgical Gynecology (Saint Petersbury, Sotis) 2:89-93 (1995).

* cited by examiner

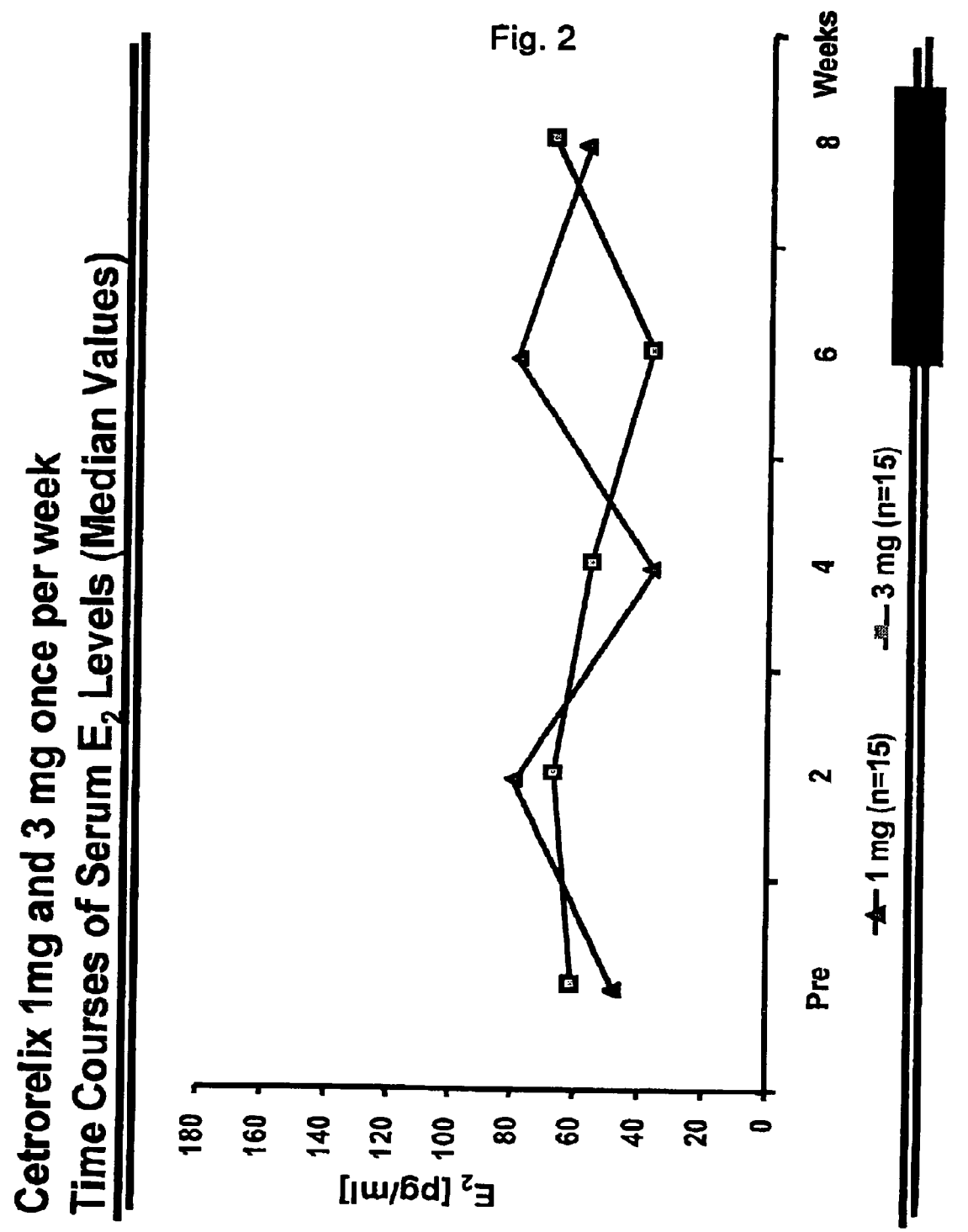

METHOD FOR THE THERAPEUTIC MANAGEMENT OF EXTRAUTERINE PROLIFERATION OF ENDOMETRIAL TISSUE, CHRONIC PELVIC PAIN AND FALLOPIAN TUBE OBSTRUCTION

REFERENCE TO RELATED APPLICATION

This application claims benefit from the Provisional Application No. 60/155,478 dated Sep. 23, 1999.

FIELD OF INVENTION

Endometriosis is one of the most frequently encountered pathologies diagnosed amongst gynecological patients. For example, between 10% and 25% of women presenting with gynecological symptoms in UK and in the USA are affected. Clinical diagnosis is made usually by laparoscopic observation of hemorrhagic or fibrotic foci on the pelvic organs. The ectopic endometrial tissue responds to ovarian hormones undergoing cyclic changes. The cyclical bleeding from the endometric deposit contributes to a local inflammatory reaction. Endometriosis commonly affects women during their childbearing years with an incidence of at least 1% (see Shaw, R. W. (1993), An Atlas of Endometriosis. The Parthenon Publishing Group).

Endometriosis is usually classified into endometriosis (genitalis) interna (adenomyosis), endometriosis genitalis externa and endometriosis extragenitalis.

Chronic pelvic pain may occur either in relation to endometriosis or as an independent disease.

Fallopian tube obstruction (FTO) is a relatively common disease and may account to for up to 20% of cases of tubal infertility (see Winfield, A. C. et al., Apparent cornual occlusion in hysterosalpingography; Reversal by glucagon. AJR Am J Roentgenol 1982; 139: 525–527).

BACKGROUND INFORMATION AND PRIOR ART

Sampson suggested that menstrual regurgitation and subsequent implantation of endometrial tissue on the peritoneal face results in endometriosis [Sampson, J. A. (1927), Peritoneal endometriosis due to menstrual dissemination of the endometrial tissue into the peritoneal cavity. Am. J. Obstet. Gynecol., 14, 422.] Several aetiologic factors may be involved in the pathogenesis of endometriosis:

Dmowski et. al. suggested that genetic and immunological factors lead to endometriosis [Dmowski, W. P. Steele, R. W. and Baker, G. F. (1981). Deficient cellular immunity in endometriosis. Am. J. Obstet. Gynecol., 141, 377] Vascular and lymphatic embolization to distant sites has been demonstrated and explains the (rare) finding of endometriosis outside the peritoneal cavity, e.g. skin, lung, kidney. Cells lining the Müllerian duct arise from primitive cells which differentiate into peritoneal cells and the cells on the surface of the ovaries. It is proposed that these adult cells undergo de-differentiation back to their primitive origin and then transform into endometrial cells [Levander, G. (1941), Bone formation by induction. An experimental study. Arch. Klin. Chir., 202, 497] Dysmenorrhea, acute or chronic pelvic pain, dyspareunia, and infertility perform the most frequent clinical symptoms reported.

FTO represents a heterogenous group of underlying pathology, preliminary intrinsic occlusion or extrinsic compression from estrogen-sensitive disorders, such as endometriosis, adenomyosis, endosalpingiosis, and myomata. FTO is frequently diagnosed by hysterosalpingography, besides laparascopy.

First choice of treatment comprises laparoscopic removal of endometric lesions. This procedure may be followed by the treatment with Danazol or LHRH agonist (for a period of six months). Women being treated with Danazol might experience gastrointestinal and hepatic disorders as well as severe androgenic side effects.

It was also proposed from a theoretical viewpoint for treatment of endometriosis and uterine myoma to use the immediate suppression by administration of a LHRH antagonist to reducing the duration of treatment and faster improvement of subjective symtoms [Th. Reissmann et al. Human Reproduction vol. 10 No. 8 pp. 1974–1981, (1995)]

Further Hodgen teaches in the U.S. Pat. No. 5,858,884 a regime for therapeutic management of a gonadal dependent condition by reducing the estrogen supply by means of long-term administration of an GnRH antagonist for 6 months or longer in an amount effective to inhibit proliferation of endometrial tissue without substantially stopping the production of endogenous estrogen. For this purpose, Hodgen teaches such a regimen or dose of GnRH antagonist to achieve a 24 hour serum estradiol level in the range of about 25 to 50 and preferably about 35 to 45 pg/ml. However, Hodgen does not describe estradiol serum levels oscillating between 60 pg/ml and 75 pg/ml. Moreover, Hodgen only teaches in the U.S. Pat. No. 5,658,884 a continuous long-term treatment (on a daily or periodic basis, the latter meaning a weekly or monthly administration) but not a short-term induction treatment for only 4 to 12 weeks. Hodgen also does not describe any combination therapy comprising the GnRH antagonist in the treatment of endometrosis. The treatment is only described on monkeys and also includes the performance of a costly and repeated progesterone challenge test to provide an 24 hour average serum estradiol level of 30 to 50 pg/ml.

As a consequence of the flare-up effect of LHRH-agonistic therapy an exacerbation of symptoms might occur during some days. Following prolonged treatment which is required to avoid the re-proliferation of endometric tissue hormonal withdrawal symptoms as well as demineralization of bones occur.

Therefore, effective drug therapy should immediately reduce the residual extrauterine endometrial tissue present after laparoscopic surgery. Duration of therapy should be only 4 to 12 weeks without the occurrence of any major hormonal withdrawal symptoms or ovarian cyst formation.

LHRH antagonists exert an immediate onset of hormonal suppression, and therefore benign gynecological tumors, such as uterine fibroids decrease within short time [Human Reproduction 1998, 13]

OBJECT OF THE INVENTION

The present invention relates to the improvement of the medical treatment of extrauterine proliferation of endometrial tissue, i.e. the administration of LHRH antagonists in patients with clinical symptoms of endometriosis, the improvement consisting of:
immediate reduction of ectopic endometrial tissue
immediate cessation of symptoms, e.g. severe pain, chronic pelvic pain and dysmenorrhea
prevention of any progress of the disease
avoidance of hormonal withdrawal symptoms
prevention of ovarian cyst formation, demineralization of bones as well as of gastrointestinal or hepatic disorders.

The inventive medical therapy can start in the early to mid follicular phase, preferably on cycle day one to three. During the treatment the estradiol serum concentration levels are kept between 35 pg/ml and 80 pg/ml, preferably between about 45–75 pg/ml, more preferably between about 50–75 pg/ml. The LHRH antagonist is administered only for 4 to 12 weeks (short-term induction treatment), either by daily, weekly or monthly administration. Following the short-term induction treatment, the administration of a contraceptive, a non-steroidal anti-rheumatic, an analgetic, an androgen other than 17-alpha-alkyl substituted testosterone or any combinations thereof is provided according to the present invention.

SUMMARY OF THE INVENTION

In the treatment of extrauterine endometrial tissue with an LHRH antagonist, therapy is started on menstrual cycle day one to three. Before starting LHRH-antagonist therapy the diagnosis is performed by laparoscopy. In cases of severe pain, LHRH antagonist therapy might be initiated without prior laparascopy.

Therapy will continue until clinical symptomatology has resolved and no proliferation of the endometrium is seen. Due to the immediate onset of suppression of the gonadotropins LH and FSH as well of sex steroids estradiol and progesterone no further proliferation of the endometrium occurs. Benign tumors or other sex steroid dependent lesions, like endometriosis decrease within four to twelve weeks of therapy. Due to the lack of flare-up no ovarian cysts develop.

Furthermore, no hormonal withdrawal symptoms are seen as the estradiol values are kept in the range of the early follicular phase of 35 to 80 pg/ml, preferably between about 45–75 pg/ml, more preferably between about 50–75 pg/ml without further increase or decrease. No titering of the dosage of the LHRH antagonist, e.g. by conducting a costly progesterone challenge test, is necessary.

The method of therapeutic management of extrauterine proliferation of endometrial tissue the improvement according to the invention therefore embraces:
immediate reduction of ectopic endometrial tissue
prevention of any progress of the disease
avoidance of hormonal withdrawal symptoms
prevention of ovarian cyst formation, demineralization of bones as well as of gastrointestinal or hepatic disorders
start of medical therapy on cycle day one to three and maintenance of estradiol levels at values of the early follicular phase throughout the entire duration of treatment by means of administration of a LHRH antagonist wherein the antagonist is preferabely cetrorelix, teverelix, ganirelix, antide or abarelix. The antagonist can also be the LHRH antagonist D-63153 (Ac-D-Nal-D-pCl-Phe-D-Pal-Ser-N-Me-Tyr-D-Hci-Nle-Arg-Pro-D-Ala-NH2) as described in the German Patent Application No. 199 11 771.3 filed on Mar. 11, 1999.

The LHRH antagonist may be given for 4 to 12 weeks in a weekly dose of 3 to 10 mg per week or for 4 to 12 weeks in a daily dose of 0.25 mg to 0.5 mg/day.

It is also possible to give the LHRH antagonist 4 to 12 weeks in a monthly dose of 12 to 40 mg per month.

In a repeat therapeutic treatment the LHRH antagonist is given for 4 to 12 weeks and the treatment is repeated two or three times a year, whereby a repeated treatment does not following directly after a short-term induction treatment. Usually a period of time of weeks or months, where no LHRH antagonist is administered, is between the end of the short-term induction treatment and the start of the repeat treatment.

To demonstrate the feasibility to maintain a low estradiol secretion under adjusted LHRH-antagonist treatment so that a therapeutic suppression occurs without withdrawal symtoms nine patients with confirmed endometriosis were treated with 3 mg of Cetrorelix acetate s.c. by weekly administration for 8 weeks. While patients compliance was excellent avoiding any hot flushes or other withdrawal symptoms and without any progress of the disease confimed by $2^{nd}$ look laparascopy the mean estradiol serum concentrations oscillated between 37 pg/ml and 64 pg/ml, preferably between 45–75 pg/ml, more preferably between about 50–75 pg/ml. Histological biopsies showed no proliferation of the endometrium at the end of treatment. No ovarian cyst formation occurred.

The FIG. 1 shows the continuous estradiol suppression to values of the early follicular phase (range of 35 pg/ml to 80 pg/ml, preferably between 45–75 pg/ml more preferably between about 50–75 pg/ml) obtained in patients with endometriosis by a weekly dose of 3 mg of Cetrorelix (LHRH antagonist) for 8 weeks. Immediate and continuous suppression of estradiol levels is obtained without any signs of estradiol withdrawal symptoms and without proliferation of the endometrium at the end of treatment.

FIG. 2 shows estradiol serum levels after administration of cetrorelix at a weekly dose of 1 mg resp. 3 mg once per week. The estradiol serum levels are between about 35–80 pg/ml, preferably between about 45–75 pg/ml, more preferably between about 50–75 pg/ml.

The endometriosis patient with distinctive symptomatic pain is suffering from a chronic disease. Surgical methods in sense of curative therapy as well as medicinal treatment to suppress the sexual steroid secretion of the patient often result only in a temporary improvement. The relapse rate of the discomforts is very high and about 70% within 5 years after finishing therapy (Schweppe, 1999).

At the same time the radical surgical therapy and the suppression of the estrogen secretion leads to considerable side effects. The radical surgical therapy in sense of hysterectomy with bilateral adnexectomy is no adequate therapy for the younger, premenopausal woman. The chronical lack of estrogen leads to the following vegetative symptoms: hot flashes, sweating, dryness of the vagina, depressive feelings and also holds the risk of osteoporosis. The alternative therapy with the synthetic steroidal compound Danazol may cause virilizing symptoms because of the androgenic effect.

Aim of the medicinal therapy of patients with endometriosis with symptomatic pain is to obtain a treatment without side effects, especially avoiding the negative effects of estrogen suppression and which is long-lasting after finishing therapy. The specific pharmacological mode of action of LHRH antagonists allows new possibilities for treatment of endometriosis.

The weekly administration of an adequate dose of an LHRH antagonist, e.g. 3 mg Cetrotide® s.c./ per week over a period of eight weeks leads to a controlled suppression of estrogen secretion so that serum concentrations between about 35 pg/ml and about 80 pg/ml, preferably between about 45–75 pg/ml, more preferably between about 50–75 pg/ml are obtained. In this serum concentration range no vegetative symptoms arise. Also the development of osteoporosis can be avoided. The symptomatic pain will be effectively suppressed in all stages of the disease (rAFS I–IV). In the stages rAFS I–II a clinical regression of the disease in sense of decrease of the implantation area is noticed (Felberbaum et. al., 2000).

In a preferred embodiment of this invention, after this treatment period of eight to twelve weeks the patient could take a contraceptive, preferably an oral contraceptive, preferably with gestagen components, unless there is a wish for pregnancy. In this connection combinations with Lynestronol 2 mg with 0.04 mg Ethinylestradiol or 2.5 mg Lynestrenol with 0.05 mg of Ethinylestradiol (e.g. Yermonil®, Lyn-ratiopharm-Sequenz®) have to be mentioned.

A combination therapy with androgens other than 17-alpha-alkyl substituted testosterones such as danazol may also be applied subsequently to the short-term induction regimen with the LHRH antagonist either alone or in combination with non-steroidal anti-rheumatics and/or analgetics. An example for a suitable androgene is halotestin™ (fluoximesterone).

The treatment with a contraceptive, preferably an oral contraceptive, preferably containing gestagens, should be individually continued until typical pain sensation occurs. In this stage the patient will have relatively small menstrual bleeding as an effect of the gestagen component of this contraceptive, preferably oral contraceptive. For covering also the especially critical pre-menstrual and menstrual days with regard to pain sensation in this phase a concomitant medication with appropriate non-steroidal anti-rheumatic drugs, e.g. diclophenac, ibuprofen, indometeacin, oxicam derivates or acetylsalicylic acid may be given. Also an analgetic such as flupirtinmaleat (Katadolon®) can be administered.

If further pain symptoms occur during this combination therapy with gestagenic contraceptives, preferably oral contraceptives, a daily, weekly or monthly therapy with the adequate dose of an LHRH antagonist as described above may be repeated. Detailed information on the respective treatment options are given below. If the patient is absolutely free of pain treatment can be changed to gestagenic contraceptive, preferably oral contraceptives, in combination with concomitant medication of appropriate non-steroid anti-rheumatic drugs or analgetics.

This therapy using the intermittent administration of an LHRH antagonist leads to a new and innovative unlimited treatment without side effects and lowers treatment burden for the patient significantly.

PHARMACEUTICAL FORMULATIONS SUITABLE FOR TREATMENT

Pharmaceutical formulations of the LHRH antagonist suitable for the therapeutic management of extrauterine proliferation of endometrial tissue, chronic pelvic pain and fallopian tube obstruction may be for example a) acetate salt formulations in the concentration of 1 mg/1 ml or lower where the powder may be dissolved in Water for Injection (WfI) or in Gluconic Acid (GA);
b) acetate salt formulations in the concentration of 1.5 mg/1 ml to 5.0 mg/1 ml, preferably 2.5 mg/1 ml where the powder may be dissolved in Water for Injection (WfI) or in Gluconic Acid (GA);
c) pamoate salt formulations in the concentration of 10 mg/1 ml to 30 mg/1 ml, preferably 15 mg/1 ml where the lyophylisate powder may be dissolved in Gluconic Acid (GA) or in Water for Injection (WfI.

According to one aspect of the present invention in the method of therapeutic management of extrauterine proliferation of endometrial tissue, chronic pelvic pain and/or fallopian tube obstruction (FTO), the improvement consisting of administration of an LHRH antagonist in the form of a short-term induction treatment for a period of about 4 to 12 weeks to a patient in need of such treatment, whereby subsequently the administration of the LHRH antagonist is ceased, is provided.

The duration of the short term induction treatment is about 4 to about 12 weeks, that means that the treatment can be between about 28 to about 84 days or from about one to about three months.

According to another aspect of the present invention in a method as mentioned above the improvement is provided, wherein the LHRH antagonist is administered such that the estrogen serum concentration level is between about 35 pg/ml and about 80 pg/ml, preferably between about 45–75 pg/ml, more preferably about 50–75 pg/ml.

According to another aspect of the present invention in a method as mentioned above the improvement is provided, characterized in that the short-term induction treatment with the LHRH antagonist is followed by administration of a contraceptive, preferably an oral contraceptive.

According to another aspect of the present invention in a method as mentioned above the improvement is provided, characterized in that the short-term induction treatment with the LHRH antagonist is followed by administration of a non-steroidal anti-rheumatic agent.

According to another aspect of the present invention in a method as mentioned is above the improvement is provided, characterized in that the short-term induction treatment with the LHRH antagonist is followed by administration of an analgetic.

According to another aspect of the present invention in a method as mentioned above the improvement is provided, characterized in that the short-term induction treatment with the LHRH antagonist is followed by administration of an androgen other than a 17-alpha-alkyl substituted testosterone.

According to another aspect of the present invention in a method as mentioned above the improvement is provided, characterized in that the short-term induction treatment with the LHRH antagonist is followed by the combined or separate administration of one or more active agents selected from the group consisting of a contraceptive, preferably an oral contraceptive, a non-steroidal anti-rheumatic agent, an analgetic, an androgen other than a 17-alpha-alkyl substituted testosterone or any combinations thereof.

According to another aspect of the present invention in a method as mentioned above the improvement is provided, characterized in that the LHRH antagonist is administered starting in the early to mid follicular phase, preferably on cycle day one to three.

According to another aspect of the present invention in a method as mentioned above the improvement is provided, characterized in that the LHRH antagonist is selected from the group consisting of cetrorelix, teverelix, ganirelix, antide, abarelix and D-63153.

According to another aspect of the present invention in a method as mentioned above the improvement is provided, characterized in that the LHRH antagonist is administered during the short-term induction treatment for 4 to 12 weeks at a weekly dose of 3 to 10 mg per week.

According to another aspect of the present invention in a method as mentioned above the improvement is provided, characterized in that the LHRH antagonist is administered during the short-term induction treatment for 4 to 12 weeks at a daily dose of 0.25 mg to 0.5 mg/day.

According to another aspect of the present invention in a method as mentioned above the improvement is provided, characterized in that the LHRH antagonist is administered during the short-term induction treatment for 4 to 12 weeks at a monthly dose of 12 to 40 mg per month.

According to another aspect of the present invention in a method as mentioned above the improvement is provided, characterized in that the LHRH antagonist is given for the induction treatment during 4 to 12 weeks and the treatment is repeated two or three times a year.

According to a further aspect of the present invention a pharmaceutical composition for treating extrauterine proliferation of endometrial tissue, chronic pelvic pain and/or fallopian tube obstruction (FTO) comprising an LHRH antagonist and optionally one or more agents selected from the group consisting of a contraceptive, preferably an oral contraceptive, a non-steroidal anti-rheumatic agent, an analgetic agent, an androgen agent other than a 17-alpha-alkyl substituted testosterone or any combinations thereof, optionally together with pharmaceutically acceptable excipients, whereby the LH-RH antagonist is administered to a patient in need thereof in a short term induction treatment for a period of about 4 to 12 weeks, then the administration of the LH-RH antagonist is ceased and optionally the one or more agents selected from the group consisting of a contraceptive, preferably an oral contraceptive, a non-steroidal anti-rheumatic agent, an analgetic, an androgen other than a 17-alpha-alkyl substituted testosterone or any combinations thereof, are administered together or separately to the patient is provided.

Suitable excipients and dosage forms are for example described by K. H. Bauer, K. H. Frömming and C. Führer, Lehrbuch der Pharmazeutischen Technologie, 6$^{th}$ edition, Stuttgart 1999, pages 163–186 (excipients) and pages 227–386 (dosage forms), including the references as cited therein.

The LH-RH antagonist can be administered for example sucutaneous (s.c.), intramuscular (i.m.) or inhalative. The agents selected from the group consisting of a contraceptive, preferably an oral contraceptive, a non-steroidal anti-rheumatic agent, an analgetic, an androgen other than a 17-alpha-alkyl substituted testosterone or any combinations thereof can be administered as known in the art (see for example the German, European or U.S. pharmacopoeia), preferably oral or inhalative.

According to another aspect of the present invention, a pharmaceutical composition as mentioned above is provided wherein the LHRH antagonist is administered such that the estrogen serum concentration level is between about 35 pg/ml and about 80 pg/ml, preferably between about 45–75 pg/ml, more preferably about 50–75 pg/ml.

According to another aspect of the present invention, a pharmaceutical composition as mentioned above is provided wherein the short-term induction treatment with the LHRH antagonist is followed by administration of a contraceptive, preferably an oral contraceptive.

According to another aspect of the present invention, a pharmaceutical composition as mentioned above is provided wherein the short-term induction treatment with the LHRH antagonist is followed by administration of a non-steroidal anti-rheumatic agent.

According to another aspect of the present invention, a pharmaceutical composition as mentioned above is provided wherein the short-term induction treatment with the LHRH antagonist is followed by administration of an analgetic.

According to another aspect of the present invention, a pharmaceutical composition as mentioned above is provided wherein the short-term induction treatment with the LHRH antagonist is followed by administration of an androgen other than a 17-alpha-alkyl substituted testosterone.

According to another aspect of the present invention, a pharmaceutical composition as mentioned above is provided wherein the short-term induction treatment with the LHRH antagonist is followed by the combined or separate administration of one or more active agents selected from the group consisting of a contraceptive, preferably an oral contraceptive, a non-steroidal anti-rheumatic agent, an analgetic, an androgen other than a 17-alpha-alkyl substituted testosterone or any combinations thereof.

According to another aspect of the present invention, a pharmaceutical composition as mentioned above is provided wherein the LHRH antagonist is administered starting in the early to mid follicular phase, preferably on cycle day one to three.

According to another aspect of the present invention, a pharmaceutical composition as mentioned above is provided wherein the LHRH antagonist is selected from the group consisting of cetrorelix, teverelix, ganirelix, antide, abarelix and D-63153.

According to another aspect of the present invention, a pharmaceutical composition as mentioned above is provided wherein the LHRH antagonist is administered during the short-term induction treatment for 4 to 12 weeks at a weekly dose of 3 to 10 mg per week.

According to another aspect of the present invention, a pharmaceutical composition as mentioned above is provided wherein the LHRH antagonist is administered during the short-term induction treatment for 4 to 12 weeks at a daily dose of 0.25 mg to 0.5 mg/day.

According to another aspect of the present invention, a pharmaceutical composition as mentioned above is provided wherein the LHRH antagonist is administered during the short-term induction treatment for 4 to 12 weeks at a monthly dose of 12 to 40 mg per month.

According to another aspect of the present invention, a pharmaceutical composition as mentioned above is provided wherein the LHRH antagonist is given for the induction treatment during 4 to 12 weeks and the treatment is repeated two or three times a year.

According to another aspect of the present invention, a pharmaceutical composition as mentioned above is provided, wherein the the one or more active agents selected from the group consisting of a contraceptive, preferably an oral contraceptive, a non-steroidal anti-rheumatic agent, an analgetic, an androgen other than a 17-alpha-alkyl substituted testosterone or any combinations thereof, are in the same or separate dosage forms.

According to another aspect of the present invention, a use of an LH-RH antagonist for the preparation of a medicament for the therapeutic management of extrauterine proliferation of endometrial tissue, chronic pelvic pain and/or fallopian tube obstruction (FTO), whereby the LHRH antagonist is administered in the form of a short-term induction treatment for a period of about 4 to 12 weeks to a patient in need of such treatment and then the administration of the LHRH antagonist is ceased, is provided.

According to another aspect of the present invention, a use of an LH-RH antagonist as mentioned above is provided wherein the LHRH antagonist is administered such that the estrogen serum concentration level is between about 35 pg/ml and about 80 pg/ml, preferably between about 45–75 pg/ml, more preferably about 50–75 pg/ml.

According to another aspect of the present invention, a use of an LH-RH antagonist as mentioned above is provided, wherein the short-term induction treatment with the LHRH antagonist is followed by administration of a contraceptive, preferably an oral contraceptive.

According to another aspect of the present invention, a use of an LH-RH antagonist as mentioned above is provided, wherein the short-term induction treatment with the LHRH antagonist is followed by administration of a non-steroidal anti-rheumatic agent.

According to another aspect of the present invention, a use of an LH-RH antagonist as mentioned above is provided, wherein the short-term induction treatment with the LHRH antagonist is followed by administration of an analgetic.

According to another aspect of the present invention, a use of an LH-RH antagonist as mentioned above is provided, wherein the short-term induction treatment with the LHRH antagonist is followed by administration of an androgen other than a 17-alpha-alkyl substituted testosterone.

According to another aspect of the present invention, a use of an LH-RH antagonist as mentioned above is provided, wherein the short-term induction treatment with the LHRH antagonist is followed by the combined or separate administration of one or more active agents selected from the group consisting of a contraceptive, preferably an oral contraceptive, a non-steroidal anti-rheumatic agent, an analgetic, an androgen other than a 17-alpha-alkyl substituted testosterone or any combinations thereof.

According to another aspect of the present invention, a use of an LH-RH antagonist as mentioned above is provided, wherein the LHRH antagonist is administered starting in the early to mid follicular phase, preferably on cycle day one to three.

According to another aspect of the present invention, a use of an LH-RH antagonist as mentioned above is provided, wherein the LHRH antagonist is selected from the group consisting of cetrorelix, teverelix, ganirelix, antide, abarelix and D-63153.

According to another aspect of the present invention, a use of an LH-RH antagonist as mentioned above is provided, wherein the LHRH antagonist is administered during the short-term induction treatment for 4 to 12 weeks at a weekly dose of 3 to 10 mg per week.

According to another aspect of the present invention, a use of an LH-RH antagonist is as mentioned above is provided, wherein the LHRH antagonist is administered during the short-term induction treatment for 4 to 12 weeks at a daily dose of 0.25 mg to 0.5 mg/day.

According to another aspect of the present invention, a use of an LH-RH antagonist as mentioned above is provided, wherein the LHRH antagonist is administered during the snort-term induction treatment for 4 to 12 weeks at a monthly dose of 12 to 40 mg per month.

According to another aspect of the present invention, a use of an LH-RH antagonist as mentioned above is provided, wherein the LHRH antagonist is given for the induction treatment during 4 to 12 weeks and the treatment is repeated two or three times a year.

According to another aspect of the present invention, a use of an LH-RH antagonist and one or more active agents selected from the group consisting of a contraceptive, preferably an oral contraceptive, a non-steroidal anti-rheumatic agent, an analgetic, an androgen other than a 17-alpha-alkyl substituted testosterone, or any combinations thereof, for the preparation of a medicament for the therapeutic management of extrauterine proliferation of endometrial tissue, chronic pelvic pain and/or fallopian tube obstruction (FTO), whereby the LHRH antagonist is administered in the form of a short-term induction treatment for a period of about 4 to 12 weeks to a patient in need of such treatment, then the administration of the LHRH antagonist is ceased and the one or more active agent selected from the group consisting of a contraceptive, preferably an oral contraceptive, a non-steroidal anti-rheumatic agent, an analgetic, an androgen other than a 17-alpha-alkyl substituted testosterone, or any combinations thereof, are administered together or separately to the patient, is provided.

According to another aspect of the present invention the use of an LH-RH antagonist and one or more active agents as mentioned above is provided, wherein the LHRH antagonist is administered such that the estrogen serum concentration level is between about 35 pg/ml and about 80 pg/ml, preferably between about 45–75 pg/ml, more preferably about 50–75 pg/ml.

According to another aspect of the present invention the use of an LH-RH antagonist and one or more active agents as mentioned above is provided, wherein the short-term induction treatment with the LHRH antagonist is followed by administration of a contraceptive, preferably an oral contraceptive.

According to another aspect of the present invention the use of an LH-RH antagonist and one or more active agents as mentioned above is provided, wherein the short-term induction treatment with the LHRH antagonist is followed by administration of a non-steroidal anti-rheumatic agent.

According to another aspect of the present invention the use of an LH-RH antagonist and one or more active agents as mentioned above is provided, wherein the short-term induction treatment with the LHRH antagonist is followed by administration of an analgetic.

According to another aspect of the present invention the use of an LH-RH antagonist and one or more active agents as mentioned above is provided, wherein the short-term induction treatment with the LHRH antagonist is followed by administration of an androgen other than a 17-alpha-alkyl substituted testosterone.

According to another aspect of the present invention the use of an LH-RH antagonist and one or more active agents as mentioned above is provided, wherein the short-term induction treatment with the LHRH antagonist is followed by the combined or separate administration of one or more active agents selected from the group consisting of a contraceptive, preferably an oral contraceptive, a non-steroidal anti-rheumatic agent, an analgetic, an androgen other than a 17-alpha-alkyl substituted testosterone or any combinations thereof.

According to another aspect of the present invention the use of an LH-RH antagonist and one or more active agents as mentioned above is provided, wherein the LHRH antagonist is administered starting in the early to mid follicular phase, preferably on cycle day one to three.

According to another aspect of the present invention the use of an LH-RH antagonist and one or more active agents as mentioned above is provided, wherein the LHRH antagonist is selected from the group consisting of cetrorelix, teverelix, ganirelix, antide, abarelix and D-63153.

According to another aspect of the present invention the use of an LH-RH antagonist and one or more active agents as mentioned above is provided, wherein the LHRH antagonist is administered during the short-term induction treatment for 4 to 12 weeks at a weekly dose of 3 to 10 mg per week.

According to another aspect of the present invention the use of an LH-RH antagonist and one or more active agents as mentioned above is provided, wherein the LHRH antagonist is administered during the short-term induction treatment for 4 to 12 weeks at a daily dose of 0.25 mg to 0.5 mg/day.

According to another aspect of the present invention the use of an LH-RH antagonist and one or more active agents as mentioned above is provided, wherein the LHRH antagonist is administered during the short-term induction treatment for 4 to 12 weeks at a monthly dose of 12 to 40 mg per month.

According to another aspect of the present invention the use of an LH-RH antagonist and one or more active agents as mentioned above is provided, wherein the LHRH antagonist is given for the induction treatment during 4 to 12 weeks and the treatment is repeated two or three times a year.

What is claimed is:

1. In the method of therapeutic management of extrauterine proliferation of endometrial tissue, chronic pelvic pain and/or fallopian tube obstruction, the improvement consisting of administration of an LHRH antagonist in the form of a short term induction treatment for a period of about 4 to 12 weeks to a patient in need of such treatment, whereby subsequently the administration of the LHRH antagonist is ceased.

2. In the method of therapeutic management of extrauterine proliferation of endometrial tissue, chronic pelvic pain and/or fallopian tube obstruction, the improvement consisting of administration of an LHRH antagonist in the form of a short term induction treatment for a period of about 4 to 12 weeks to a patient in need of such treatment, wherein the LHRH antagonist is administered in a dosage to achieve the estrogen serum concentration level between about 35 pg/ml and about 80 pg/ml, whereby subsequently the administration of the LHRH antagonist is ceased.

3. A method according to claim 1 wherein the short-term induction treatment with the LHRH antagonist is followed by administration of a contraceptive.

4. A method according to claim 1 wherein the short-term induction treatment with the LHRH antagonist is followed by administration of a non-steroidal anti-rheumatic agent.

5. A method according to claim 1 wherein the short-term induction treatment with the LHRH antagonist is followed by administration of an analgetic.

6. A method according to claim 1 wherein the short-term induction treatment with the LHRH antagonist is followed by administration of an androgen other than a 17-alpha-alkyl substituted testosterone.

7. A method according to claim 1 wherein the short-term induction treatment with the LHRH antagonist is followed by the combined or separate administration of one or more active agents selected from the group consisting of a contraceptive, a non-steroidal anti-rheumatic agent, an analgesic, an androgen other than a 17-alpha-alkyl substituted testosterone or any combinations thereof.

8. A method according to claim 1 wherein the LHRH antagonist is administered starting in the early to mid follicular phase.

9. A method according to claim 1 wherein the LHRH antagonist is selected from the group consisting of cetrorelix, teverelix, ganirelix, antide, abarelix and Ac-D-Nal-D-pCl-Phe-D-Pal-Ser-N-Me-Tyr-D-Hci-Nle-Arg-Pro-D-Ala-NH2 LRHR antagonist.

10. A method according to claim 1 wherein the LHRH antagonist is administered during the short-term induction treatment for about 4 to 12 weeks at a weekly dose of about 3 to 10 mg per week.

11. A method according to claim 1 wherein the LHRH antagonist is administered during the short-term induction treatment for about 4 to 12 weeks at a daily dose of about 0.25 mg to 0.5 mg/day.

12. A method according to claim 1 wherein the LHRH antagonist is administered during the short-term induction treatment for about 4 to 12 weeks at a monthly dose of about 12 to 40 mg per month.

13. A method according to claim 1 wherein the LHRH antagonist is given for the induction treatment during about 4 to 12 weeks and the treatment is repeated two or three times a year.

14. A method according to claim 2, wherein said estrogen serum concentration level is between about 45–75 pg/ml.

15. A method according to claim 14, wherein said estrogen serum concentration level is about 50 to about 75 pg/ml.

16. A method according to claim 3, wherein said contraceptive is an oral contraceptive.

17. A method according to claim 8, wherein the LHRH antagonist is administered on cycle day one to three.

* * * * *